United States Patent [19]

Muggli

[11] Patent Number: 4,873,020

[45] Date of Patent: Oct. 10, 1989

[54] FLUOROCHEMICAL SURFACTANTS AND PROCESS FOR PREPARING SAME

[75] Inventor: Imelda A. Muggli, St. Paul, Minn.

[73] Assignee: Minnesota Mining and Manufacturing Company, St. Paul, Minn.

[21] Appl. No.: 253,136

[22] Filed: Oct. 4, 1988

[51] Int. Cl.⁴ .................. B01F 17/16; C11D 3/26
[52] U.S. Cl. .................. 252/355; 252/542; 252/544; 252/545; 252/353; 544/71; 544/108; 562/83
[58] Field of Search .......... 252/355, 545, 542, 544, 252/353; 544/71, 108; 260/501.15

[56] References Cited

U.S. PATENT DOCUMENTS

| | | | |
|---|---|---|---|
| 2,759,019 | 8/1956 | Brown et al. | 260/556 |
| 2,809,990 | 10/1957 | Brown | 260/534 |
| 3,147,064 | 9/1964 | Brown et al. | 8/116.2 |
| 3,723,512 | 3/1973 | Niederprum et al. | 260/501.15 |
| 4,006,064 | 2/1977 | Niederprum et al. | 204/51 |
| 4,028,257 | 6/1977 | Thompson | 252/8.55 C |
| 4,168,277 | 9/1979 | Mitschke et al. | 260/501.15 |
| 4,203,850 | 5/1980 | Wirtz et al. | 252/8.05 |
| 4,222,828 | 9/1980 | Zuurdeeg | 204/16 |
| 4,313,978 | 2/1982 | Stevens et al. | 427/384 |

*Primary Examiner*—Paul Lieberman
*Assistant Examiner*—Susan Franklin

*Attorney, Agent, or Firm*—D. M. Sell; W. N. Kirn; C. Truesdale

[57] ABSTRACT

Fluorochemical surfactant compositions are provided. The compositions comprise a fluorochemical amine salt which can be represented by the formula:

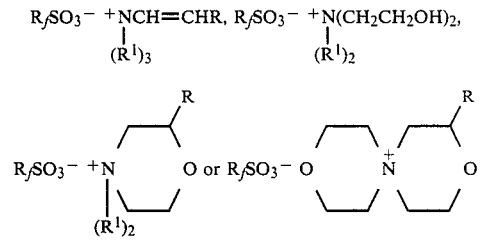

wherein $R_f$ is a perfluoroaliphatic radical containing 3 to 20 carbon atoms, R is H or $CH_3$, and $R^1$ is an alkyl radical containing 1 to 4 carbon atoms. The fluorochemical surfactant compositions are prepared by reacting at least one perfluoroalkyl sulfonyl fluoride having 3 to 20 alkyl carbon atoms, ethylene or propylene oxide, and at least one tertiary amine, $(R^1)_3N$ wherein $R^1$ is an alkyl radical having 1 to 4 carbon atoms and which may contain a hydroxyl group.

8 Claims, No Drawings

FLUOROCHEMICAL SURFACTANTS AND PROCESS FOR PREPARING SAME

This invention relates to fluorochemical surfactants and to a process for preparing such fluorochemical surfactants.

Fluorochemical surfactants are well-known for their ability to provide improved wetting, spreading, and leveling in a wide variety of systems. Some typical application areas include floor polishes, alkaline cleaners, leak-detection solutions, corrosion inhibitors, specialty inks, and in processes varying from photographic development and electroplating to the manufacture of clay refractories.

Among the early fluorochemical surfactants are the fluorocarbon dialkylamines and their corresponding quaternary ammonium derivatives disclosed in U.S. Pat. No. 2,759,019 (Brown et al.), the perfluoroalkanesulfonamido alkylenemonocarboxylic acids disclosed in U.S. Pat. No. 2,809,990 (Brown), and the N-perfluoroalkylsulfonamidoalkyl halomethylethers and quaternized derivatives thereof disclosed in U.S. Pat. No. 3,147,064 (Brown et al.).

Later, U.S. Pat. No. 4,006,064 (Niederprum et al.) disclosed, as a fluorine-based surfactant, a quaternary ammonium perfluoroalkane sulfonate of the formula $[R_fSO_3]^- [NR^1R^2R^3R^4]^+$ in which $R^1$, $R^2$, $R^3$, and $R^4$ each individually is alkyl, alkenyl, cycloalkyl, or aralkyl of up to 18 carbon atoms, or two or three of $R^1$, $R^2$, $R^3$, and $R^4$ together with the nitrogen atom to which they are attached form a heterocyclic ring, and $R_f$ is a perfluorinated alkyl radical with 6 to 12 carbon atoms. Niederprum et al. state that this surfactant is useful in electrodeposition of a chrome layer wherein the chrome is deposited from an electrolyte solution containing a hexavalent chromium compound.

U.S. Pat. No. 4,028,257 (Thompson) discloses a perfluorinated compound represented by the formula $[C_8F_{17}SO_2NHC_3H_6N(CH_3)_3]^+A^-$ wherein $A^-$ is $Cl^-$, $I^-$, $F^-$, or $Br^-$, which is used together with an adduct of trimethyl-1-heptanol plus seven moles of ethylene oxide to lower the surface tension of various aqueous-based liquids, e.g. acids, spent acids, brines, water, etc. and corresponding gelled liquids, when such fluids are employed in environments where they come in contact with earthen formations.

U.S. Pat. No. 4,168,277 (Mitschke et al.) discloses a process for the production of tetraethyl ammonium perfluoroalkyl sulphonates $(C_2H_5)_4N^+R_fSO_3^-$, wherein $R_f$ represents a perfluorinated alkyl radical with about 4 to 10 carbon atoms, by reacting crude perfluoroalkyl sulphonic acid fluoride which has not been especially purified, with triethylamine and an ethoxy silane in an inert solvent at temperatures of about 10° to 60° C. Mitschke et al. show, for example, the following reaction equation

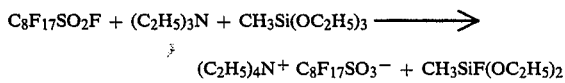

$$(C_2H_5)_4N^+ C_8F_{17}SO_3^- + CH_3SiF(OC_2H_5)_2$$

These tetraethyl ammonium perfluoroalkyl sulphonates are described as being useful for suppressing chromium mist in electro-chromium plating, as an internal mold-release agent in the injection molding of thermoplasts, as wetting agents in the acid polishing of glass and in photographic emulsions.

U.S. Pat. No. 4,203,850 (Wirtz et al.) disclose fluorochemical surfactants which have the formula $R_f$—CF═CH—CH_2—$^{(+)}$N—$R_4R_5R_6$ in which $R_f$ is a perfluoroalkyl group having from 3 to 16 carbon atoms, $R_4$ is a hydrogen atom, a $C_{1-4}$ alkyl, cyclohexyl or 2-hydroxyalkyl having from 2 to 6 carbon atoms, $R_5$ is a $C_{1-4}$ alkyl radical, a cyclohexyl radical or 2-hydroxyalkyl having from 2 to 6 carbon atoms, and $R_6$ is a water-solubilizing radical, —Q—$R_7$ with Q being an alkylene group having from 2 to 6 carbon atoms and $R_7$ being a water-solubilizing polar group such as —$CO_2^-$, —$SO_2^-$, —$SO_3^-$, $OP(H)O_2^-$, and especially $OSO_3^-$. These surfactants are described as being useful in foam extinguishing agents.

U.S. Pat. No. 4,222,828 (Zuurdeeg) discloses a process for electro-depositing inorganic particles and a metal on a surface which utilizes fluorochemical surfactants having the structural formulae

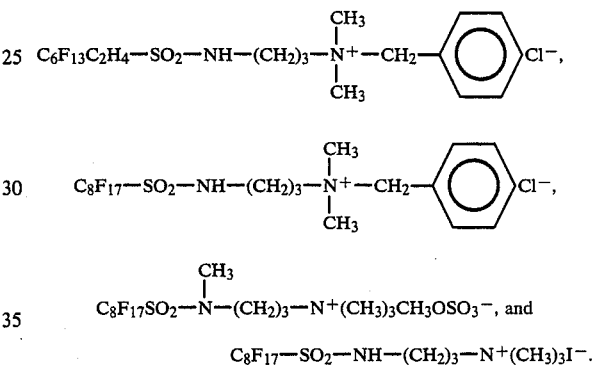

$$C_8F_{17}SO_2-N(CH_3)-(CH_2)_3-N^+(CH_3)_3CH_3OSO_3^-, \text{ and}$$

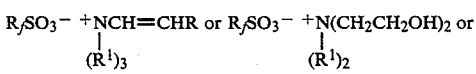

U.S. Pat. No. 4,313,978 (Stevens et al.) discloses a method of treating a surface to reduce the static charging thereon by applying an antistatic composition comprising a fluorinated anionic surfactant which is an amine salt of an acid containing a fluorinated organic radical and an antistatic agent which is an ionic salt of an amine. The preferred surfactants are depicted by the formula $R_fAX^-Z^+$ in which $R_f$ represents a fluorinated organic radical, A represents a bond or a divalent linking group, $X^-$ represents an acid anion, and $Z^+$ represents a quaternary ammonium cation.

Although the above-discussed fluorochemical surfactants are generally useful in the systems for which they are selected, there has been a need for fluorochemical surfactants which have improved surface tension depressant properties and which can be easily and economically produced.

The present invention provides fluorochemical surfactant compositions which have useful surface tension depressant properties and a method for producing such fluorochemical surfactant compositions easily and economically.

The fluorochemical surfactant compositions of the present invention comprise at least one fluorochemical amine salt which can be represented by the formula:

$$R_fSO_3^- \;\; ^+\!\!\underset{(R^1)_3}{N}CH=CHR \text{ or } R_fSO_3^- \;\; ^+\!\!\underset{(R^1)_2}{N}(CH_2CH_2OH)_2 \text{ or}$$

-continued

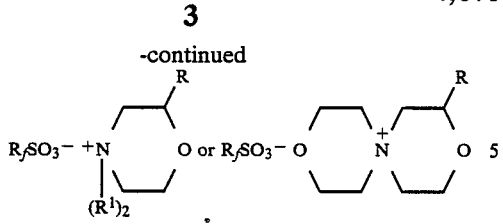

wherein R is H or CH$_3$, each R$^1$ is independently an alkyl radical containing 1 to 4 carbon atoms and may also contain a hydroxyl group, and R$_f$ is a perfluoroaliphatic radical containing 3 to 20, preferably 6 to 10, carbon atoms and can be straight chain, branched chain, or, if sufficiently large, cyclic, or combinations thereof, such as alkylcycloaliphatic radicals.

The compositions which comprise the fluorochemical amine salt represented by the formula

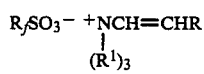

may further comprise a fluorochemical amine salt which can be represented by the formula

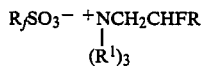

wherein R, R$^1$, and R$_f$ are as defined above.

Typical cations of the salts of this invention include, for example,

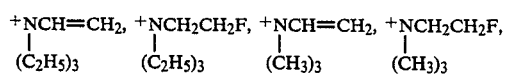

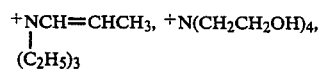

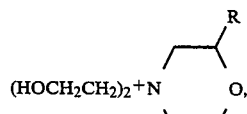

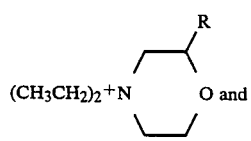

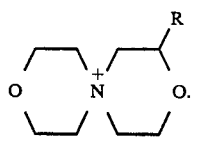

The skeletal chain in the fluoroaliphatic radical can include catenary oxygen, hexavalent sulfur, and/or trivalent nitrogen hetero atoms bonded only to carbon atoms, such hetero atoms providing stable linkages between fluorocarbon portions of R$_f$ and not interfering with the inert character of the R$_f$ radical. The fluoroaliphatic radical, R$_f$, generally is a fluorinated, stable, inert, non-polar, preferably saturated, monovalent moiety which is both oleophobic and hydrophobic. Preferably R$_f$ is C$_n$F$_{2n+1}$— where n is 6 to 10. The fluorochemical surfactant compositions may also contain small amounts of fluoroaliphatic sulfonate salts having unknown cationic structures.

These fluorochemical surfactant compositions are useful as wetting agents, dispersing agents, foaming and defoaming agents, and antistatic agents, and are particularly useful as surfactants and emulsifiers.

The method of producing fluorochemical surfactant compositions of the present invention comprises reacting at least one perfluoroalkyl sulfonyl fluoride having 3 to 20 alkyl carbon atoms, preferably perfluorooctane or perfluorodecane sulfonyl fluoride, ethylene oxide, or propylene oxide, and at least one tertiary amine, (R$^1$)$_3$N, wherein R$^1$ is an alkyl radical having 1 to 4 carbon atoms and which may contain a hydroxyl group. Preferably, the reaction is carried out at a temperature of about 60° to 150° C., more preferably about 90° to 100° C., for a period of about 2 to 16 hours.

This reaction can be represented by the following reaction schemes:

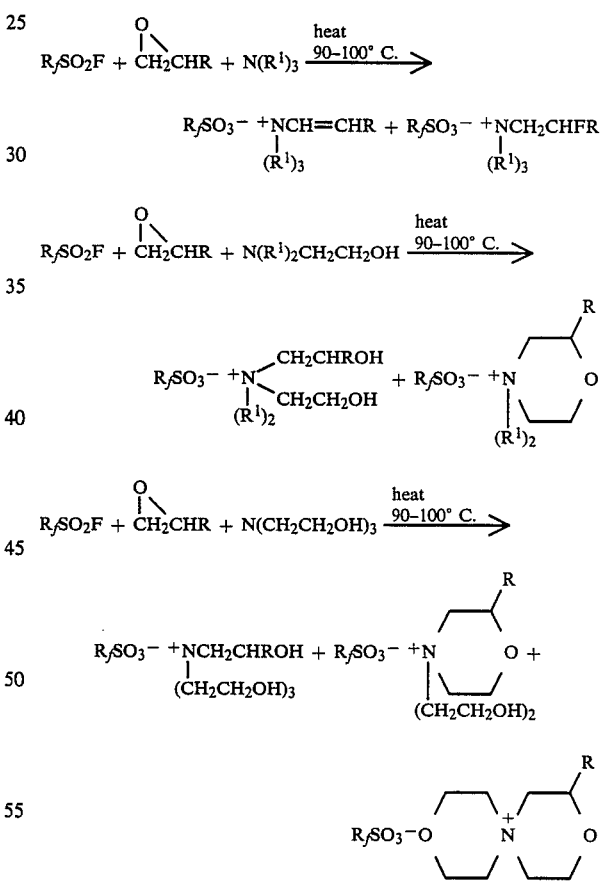

where R$^1$ and R$_f$ are as previously defined and R is H or CH$_3$. Further reaction of the mixture of

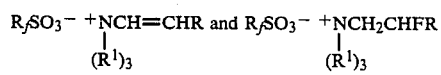

with a strong base such as sodium methylate results in a composition substantially exclusively of

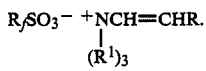

The strong base preferably has a pKa value of at least 15.

This invention will now be illustrated by the following non-limiting examples.

EXAMPLE 1

Into a 350 mL pressure vessel were charged, 48.5 g (0.1 mole) perfluorooctane sulfonyl fluoride, 4.41 g (0.1 mole) ethylene oxide, and 10.12 g (0.1 mole) triethylamine. The vessel was closed and heated to 90° C. with agitation for 12 hours. The vessel was maintained at 90° C. with continuous agitation. The vessel was cooled and the reaction product was dissolved in methylene chloride. The crude yield was 98%. The solution was washed with a small amount of water and dried. The resulting fluorochemical surfactant product was a yellow waxy solid obtained at a yield of 70%. Analysis of the product by H and F nuclear magnetic resonance (NMR) and fast atom bombardment mass spectroscopy confirmed the presence of

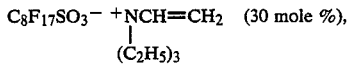

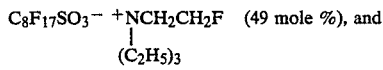

21 mole % of fluoroaliphatic sulfonate amine salts having unknown cationic structure.

EXAMPLE 2

A fluorochemical surfactant was prepared as in Example 1 using as reactants 48.5 g (0.1 mole) perfluorooctane sulfonyl fluoride, 4.41 g (0.1 mole) ethylene oxide, and 5.91 g (0.1 mole) trimethylamine with the reaction temperature being held at 90° C. for 7 hours. The reaction product was cooled and dissolved in about 100 mL methanol. The crude yield was 77%. The methanol was evaporated to yield a brown waxy solid. Analysis of the product by H and F NMR confirmed the presence of

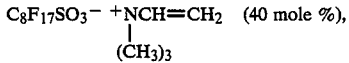

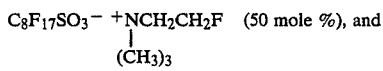

10 mole % of fluoroaliphatic sulfonate amine salts having unknown cationic structure.

EXAMPLE 3

A fluorochemical surfactant was prepared as in Example 1 using as reactants 146.25 g (0.25 mole) perfluorodecane sulfonyl fluoride, 11.01 g (0.25 mole) ethylene oxide, and 25.3 g (0.25 mole) triethylamine with the reaction temperature being 100° C. and the reaction continuing for 12 hours. The reaction product was cooled and 178 g (97.5% yield) crude product was collected. Twenty grams of the crude product were dissolved in 30 mL xylene hexafluoride with heating and this solution was washed with water. Phase separation was carried out and the organic phase was dried over magnesium sulfate. The solvent was stripped off and 16 g (78% yield) of a waxy tan solid was obtained. Analysis of the product by H and F NMR confirmed the presence of

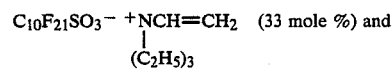

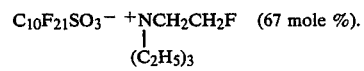

EXAMPLE 4

Into a 100 mL flask equipped with a heating mantle, a stirrer, and a reflux condenser were placed 20 g (0.0276 mole) of the crude fluorochemical surfactant of Example 3 and 10 mL methanol which were heated to about 50° C. to dissolve the fluorochemical surfactant. To this solution were added 2.5 g (0.046 mole) sodium methylate (provided as a 25 weight percent solution in methanol) and the reaction mixture was allowed to reflux for 2 hours. The methanol was distilled off under reduced pressure and the resultant product was dissolved in 40 mL xylene hexafluoride with heating. This xylene hexafluoride solution was washed with 10 mL deionized water and the resulting phases were separated. The xylene hexafluoride was distilled off under reduced pressure to yield 14.2 g of a yellow, slightly waxy material. Analysis of the product by H and F NMR confirmed the presence of 100 mole %

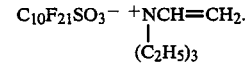

EXAMPLE 5

A fluorochemical surfactant was prepared as in Example 1 using as reactants 121.25 g (0.25 mole) perfluorooctane sulfonyl fluoride, 44.04 g (1.0 mole) ethylene oxide, and 25.33 g (0.25 mole) triethylamine with the reaction temperature raised to 100° C. and held at 100° C. for 16 hours. The reaction product was cooled and 187 g (98% yield) of a thick brown product was recovered. Twenty-five grams of the product was dissolved in 40 mL methylene chloride and the solution was washed with water. The product was dried and the solvent ws stripped off to yield a waxy brown product (18.2 g, 71% yield). Analysis of the major product by H and F NMR and liquid chromatography confirmed the presence of

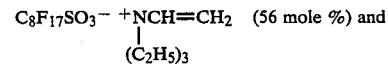

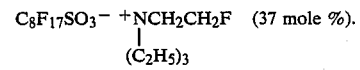

Analysis also showed about 7 mole % of minor products including $C_8F_{17}SO_3^- \ ^+NCH_2CH_2OCH_2CH_2F$
         |
       $(C_2H_5)_3$

EXAMPLE 6

A fluorochemical surfactant was prepared as in Example 1 using as reactants 121.5 g (0.25 mole) perfluorooctane sulfonyl fluoride, 14.5 g (0.25 mole) propylene oxide, and 25.33 g (0.25 mole) triethylamine with the reaction temperature being raised to 100° C. and then held at 100° C. for 30 hours. The reaction mixture was cooled and 159 g (99% yield) of a dark viscous product was recovered. Twenty grams of the product was dissolved in 40 mL methylene chloride, washed with water, and dried. After solvent stripping, 14.7 g (73% yield) of a waxy brown product was recovered. Analysis of the product by H and F NMR confirmed the presence of $C_8F_{17}SO_3^- \ ^+NCH=CHCH_3$ (58 mole %) and
         |
       $(C_2H_5)_3$ $C_8F_{17}SO_3^- \ ^+NCH_2CHFCH_3$ (42 mole %).
         |
       $(C_2H_5)_3$

EXAMPLE 7

A fluorochemical surfactant was prepared as in Example 1 using as reactants 146.25 g (0.25 mole) perfluorodecane sulfonyl fluoride, 11.01 g (0.25 mole) of ethylene oxide, and 37.3 g (0.25 mole) triethanolamine with the reaction temperature being 95° C. and the reaction continuing for 8 hours. The reaction product was cooled and 193 g (99% yield) crude product was collected. 10 g of the crude product was dissolved in methanol with heating and a small amount of product formed a white precipitate. The precipitate was filtered off yielding 0.6 g (6%) of a white, hard, waxy material. The methanol was stripped off the solvent-soluble portion and 7.9 g (78% yield) of a yellow, sticky wax was obtained. Analysis of the yellow wax product by H and F NMR and fast atom bombardment mass spectroscopy indicated the presence of

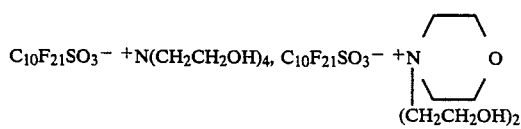

$C_{10}F_{21}SO_3^- \ ^+N(CH_2CH_2OH)_4$, $C_{10}F_{21}SO_3^- \ ^+N\langle O(CH_2CH_2OH)_2\rangle$ and a structure containing spiromorpholine cations,

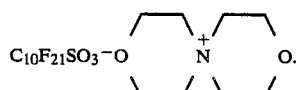

EXAMPLE 8

A fluorochemical surfactant was prepared as in Example 1 using as reactants 146.25 g (0.25 mole) perfluorodecane sulfonyl fluoride, 11.01 g (0.25 mole) ethylene oxide, and 29.3 g (0.25 mole) N,N-diethylethanolamine with the reaction temperature being 100° C. and the reaction continuing for 16 hours. The reaction product was cooled and 176 g (94% yield) of crude product was collected. 10 g of the crude product was dissolved in 40 g of ethanol with heating. A portion of the crude product was not soluble and formed a precipitate. The precipitate was filtered off, yielding, after drying, 2.67 g (25.1% yield) of a yellow powder. The methanol was stripped off the solvent-soluble portion and 5.8 g (55.0% yield) of a dark brown sticky wax was obtained. Analysis of the wax by H and F NMR indicated the presence of

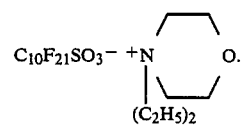

Surface Tension Evaluation

Aqueous solutions containing 50 ppm, 100 ppm, 200 ppm, and 400 ppm of each of the above-prepared fluorochemical surfactant compositions were prepared and tested for static surface tension at equilibrium at 22° C. using a Surface Tensiomat ™, Model 21 available from Fisher Scientific Co. The results are set forth in Table I. For Comparative Examples C1–C3, fluorochemical surfactants $C_8F_{17}SO_3^--NH_4^+$, and $C_8F_{17}SO_3^--H_2N(C_2H_4OH)_2^+$ and $C_8F_{17}SO_3^--N(C_2H_5)_4^+$ (Example 1 of U.S. Pat. No. 4,006,064), respectively, were tested for static surface tension at equilibrium in the same manner as the fluorochemical surfactant of Example 1. For Comparative Example C4, a stock solution was prepared using 4 parts of a 25 weight percent solution of $C_{10}F_{21}SO_3^-$$^+NH_4$ in 50:50 by weight of ethyleneglycol monobutyl ether and water, 4 parts dipropylene glycol monomethyl ether, and 92 parts deionized water and aqueous solutions containing 50 ppm, 100 ppm, 200 ppm, and 400 ppm $C_{10}F_{21}SO_3^-$$^+NH_4$ were prepared using the stock solution and tested for static surface tension at equilibrium. The results are set forth in Table 1.

TABLE I

| Surfactant of Example Number | Static Surface Tension (dynes/cm @ conc.) | | | |
|---|---|---|---|---|
| | 50 ppm | 100 ppm | 200 ppm | 400 ppm |
| 1 | 31.0 | 23.5 | 20.5 | 20.5 |
| 2 | 32.0 | 24.5 | 22.5 | 19.5 |
| 3 | 24.6 | 20.9 | 19.3 | 18.8 |
| 4 | 25.3 | 18.3 | 18.4 | 18.5 |
| 5 | 34.6 | 31.8 | 29.3 | 22.2 |
| 6 | 40.1 | 34.2 | 26.8 | 20.9 |
| 7 | 25.0 | 21.3 | 19.5 | 18.7 |
| 8 | 25.3 | 21.7 | 19.5 | 18.5 |
| C1 | 47.0 | 37.5 | 32.0 | 26.5 |
| C2 | 44.0 | 36.5 | 27.5 | 24.0 |
| C3 | 46.5 | 39.5 | 30.0 | 27.5 |
| C4 | 32.0 | 24.0 | 22.6 | 21.3 |

As can be seen from the data in Table I, the fluorochemical surfactant compositions of the invention provide a greater reduction in surface tension than do the comparative fluorochemical ammonium or amine perfluoroalkane sulfonate salt surfactants having the same number of carbon atoms in the sulfonate anion at comparable concentration levels.

It will be appreciated that the instant specification and examples are set forth by way of illustration and not limitation, and that various modifications and changes may be made without departing from the spirit and scope of the present invention.

What is claimed is:

1. Fluorochemical surfactant compositions comprising at least one fluorochemical amine salt which can be represented by the formula:

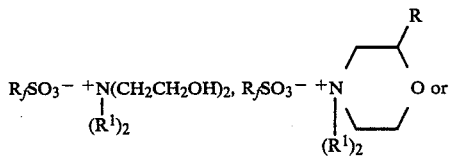

wherein $R_f$ is a perfluoroaliphatic radical containing 3 to 20 carbon atoms, R is H or $CH_3$, and each $R^1$ is independently an alkyl radical containing 1 to 4 carbon atoms.

2. The composition of claim 1 wherein $R^1$ is methyl, ethyl, or propyl.

3. The composition of claim 1 wherein $R^1$ contains a hydroxyl group.

4. Fluorochemical surfactant compositions comprising the reaction product of at least one perfluoroalkyl sulfonyl fluoride having 3 to 20 alkyl carbon atoms, ethylene or propylene oxide, and at least one tertiary amine, $(R^1)_3N$ wherein $R^1$ is an alkyl radical having 1 to 4 carbon atoms and with the proviso that at least two alkyl radicals contain hydroxyl groups.

5. The composition of claim 4 wherein said perfluoroalkyl sulfonyl fluoride is perfluorooctane or perfluorodecane sulfonyl fluoride, and said tertiary amine is triethanol amine.

6. The composition of claim 4 wherein said perfluoroalkyl sulfonyl fluoride is perfluorooctane or perfluorodecane sulfonyl fluoride, and said tertiary amine is N,N-diethylethanolamine.

7. A process for producing fluorochemical surfactant compositions comprising reacting (a) at least one perfluoroalkyl sulfonyl fluoride having 3 to 20 alkyl carbon atoms, (b) ethylene or propylene oxide, and (c) a trialkanol amine, the alkanol groups of which have 1 to 4 carbon atoms.

8. A process for producing fluorochemical surfactant compositions comprising reacting (a) at least one perfluoroalkyl sulfonyl fluoride having 3 to 20 alkyl carbon atoms, (b) ethylene or propylene oxide, and (c) a dialkylalkanol amine, the alkyl and alkanol groups of which have 1 to 4 carbon atoms.

* * * * *

UNITED STATES PATENT AND TRADEMARK OFFICE
CERTIFICATE OF CORRECTION

PATENT NO. : 4,873,020

DATED : October 10, 1989

INVENTOR(S) : Imelda A. Muggli

It is certified that error appears in the above-identified patent and that said Letters Patent is hereby corrected as shown below:

On the title page, Abstract Formula should read as follows:

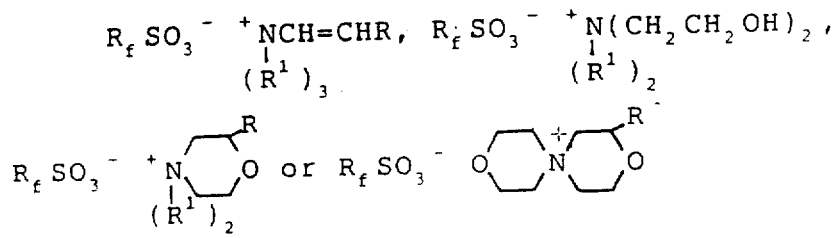

Col. 2, line 19, "electro-depositing" should read -- electro-codepositing --

Signed and Sealed this

Fifth Day of March, 1991

Attest:

HARRY F. MANBECK, JR.

Attesting Officer

Commissioner of Patents and Trademarks